United States Patent [19]

Johlin, Jr.

[11] Patent Number: 5,556,388
[45] Date of Patent: Sep. 17, 1996

[54] SAFETY RETENTION AND RECAPPING DEVICES FOR HYPODERMIC NEEDLES/INTRAVENOUS INJECTION/PORTS

[75] Inventor: Frederick C. Johlin, Jr., Iowa City, Iowa

[73] Assignee: Advanced Medical Concepts Incorporated, Iowa City, Iowa

[21] Appl. No.: 195,568

[22] Filed: Feb. 14, 1994

Related U.S. Application Data

[63] Continuation of Ser. No. 893,493, Jun. 4, 1992, abandoned.

[51] Int. Cl.⁶ ................................................. A61M 5/00
[52] U.S. Cl. ........................... 604/263; 128/919; 206/364; 206/370
[58] Field of Search ................................... 604/187, 192, 604/263; 128/919, 917; 33/403–405, 411, DIG. 10; 206/365–366, 363–364, 367–370, 388, 49, 443, 486–490; 294/1.1, 2, 10; 312/209

[56] References Cited

U.S. PATENT DOCUMENTS

| | | | |
|---|---|---|---|
| 3,696,920 | 10/1972 | Lahay | 206/370 |
| 3,948,390 | 4/1976 | Ferreri | 206/370 |
| 4,596,562 | 6/1986 | Vernon | 604/192 |
| 4,717,386 | 1/1988 | Simmons | 604/192 |
| 4,801,166 | 1/1989 | Jordan et al. | 294/9 |
| 4,826,003 | 5/1989 | Levy | 206/45.31 |
| 4,844,249 | 7/1989 | Coulombe | 206/438 |
| 4,846,803 | 7/1989 | Emerson | 604/263 |
| 4,852,844 | 8/1989 | Villaveces | 248/314 |
| 4,950,015 | 8/1990 | Nejib et al. | 294/19.1 |
| 5,013,299 | 5/1991 | Clark | 604/114 |
| 5,024,666 | 6/1991 | Pituch | 604/263 |
| 5,099,992 | 3/1992 | Heimreid | 206/366 |
| 5,112,314 | 5/1992 | Aragon et al. | 604/192 |
| 5,156,426 | 10/1992 | Graves | 294/1.1 |
| 5,160,324 | 11/1992 | Halbach | 604/192 |
| 5,435,448 | 7/1995 | Kempen | 206/370 |

*Primary Examiner*—Corrine M. McDermott
*Attorney, Agent, or Firm*—Woodard, Emhardt, Naughton, Moriarty & McNett

[57] ABSTRACT

A set of safety retention and recapping devices for intravenous injection ports and hypodermic needles are disclosed. In one such device, a retainer for holding a hypodermic needle and needle cover adjacent an intravenous injection port and associated tubing is provided which lockably receives a needle cover and also lockably receives an intravenous injection port and associated intravenous tubing in convenient adjacency thereto. The safety retention device further includes means for being adjustably located onto a vertical intravenous equipment support pole. A second pocketsized device is disclosed which is readily portable and adapted for single hand use. A third device includes a restraint for attachment to the arm of a patient. A fourth device incorporates a mounting which provides secure bedside attachment and includes a flange that slides under the mattress of a bed, with the device being thus held in a convenient location for use by the weight of the mattress.

2 Claims, 5 Drawing Sheets

SAFETY RETENTION AND RECAPPING DEVICES FOR HYPODERMIC NEEDLES/INTRAVENOUS INJECTION/PORTS

This application is a continuation of application Ser. No. 07/893,493, filed Jun. 4, 1992, now abandoned.

BACKGROUND OF THE INVENTION

This invention relates generally to safety devices for use with hypodermic needles. More specifically, this invention relates to retention devices for holding and recapping hypodermic needles for reuse in administering unit dose medication through an intravenous injection port.

Inadvertent needle prick injuries occurring during recapping of hypodermic needles have long been problematic in the medical profession. As a result, various devices have been developed for holding needle caps remote from a user. These devices permit reinsertion of the hypodermic needle in the needle cap with reduced risk of needle prick injury to the user. Nevertheless, because of either their complexity and cost, or their inconvenience, these devices have not been widely used in the medical community. Medical personnel have instead generally resorted to merely discarding uncapped hypodermic needles that have been used rather than taking the extra safety step of recapping the used needles for reuse or disposal. While this approach provides one solution to the risk of injury during use, the discarding of unprotected needles may nonetheless produce inadvertent needle prick injuries during the handling of hospital waste products. Additionally, the failure to reuse hypodermic needles where reuse is appropriate, such as in unit dose medication through intravenous injection ports, increases the numbers of new hypodermic needles which need to be made, thus tending to drive up the cost of health care.

Hypodermic needles are routinely used for unit dosing of medication, where needles are repeatedly inserted into intravenous injection ports of associated intravenous infusion tubing for repeated administration of small doses of medication. For the above mentioned reasons, hypodermic needles are currently either being reused during unit dosing without being recapped, thus increasing the risk of needle prick injury, or they are discarded after each unit dose has been administered, having the effect of increasing the cost of medical care without satisfactorily removing the risk of injury.

A need therefore exists for an improved needle and needle cap retainer. Such a device would facilitate safe recapping of used hypodermic needles by reducing inadvertent needle prick injuries. A need also exists for a needle and needle cap retainer which provides safe manipulation of used hypodermic needles in conjunction with intravenous infusion tubing. Such a device would allow hypodermic needles to be safely used during repeated administration or unit dosing of medication.

SUMMARY OF THE INVENTION

Generally speaking, the present invention provides retention and recapping devices which enhance the safety and convenience of using and recapping hypodermic needles in conjunction with intravenous injection ports. A set of such devices are disclosed.

In one such device, a retainer for holding a hypodermic needle and needle cover adjacent an intravenous injection port and associated tubing is provided which lockably receives a needle cover and also lockably receives an intravenous injection port and associated intravenous tubing in convenient adjacency thereto. The safety retention device further includes means for being adjustably located onto a vertical intravenous equipment support pole. In a second embodiment, a pocketsized retainer is disclosed which is conveniently portable and specially adapted for single hand use. According to a third embodiment, a device includes a restraint for attachment to the arm of a patient. In yet another disclosed embodiment, a mounting is incorporated which provides secure bedside attachment and includes a flange that slides under the mattress of a bed, with the device being thus held in a convenient location for use by the weight of the mattress.

One object of the present invention is to provide an improved hypodermic needle and needle cover retainer.

Another object of the present invention is to provide a hypodermic needle and needle cover retainer which facilitates safe universal hypodermic needle recapping.

Another object of the present invention is to provide a hypodermic needle and needle cover retainer which increases the safety of inserting needles into intravenous injection ports associated with intravenous infusion tubing.

Still yet another object of the present invention is to provide a hypodermic needle and needle cover retainer which allows for safe reuse of hypodermic needles during unit dosing of medication.

Other related objects and advantages of the present invention will become apparent from the following drawings and written description.

DESCRIPTION OF THE PREFERRED EMBODIMENT

Figure 1:
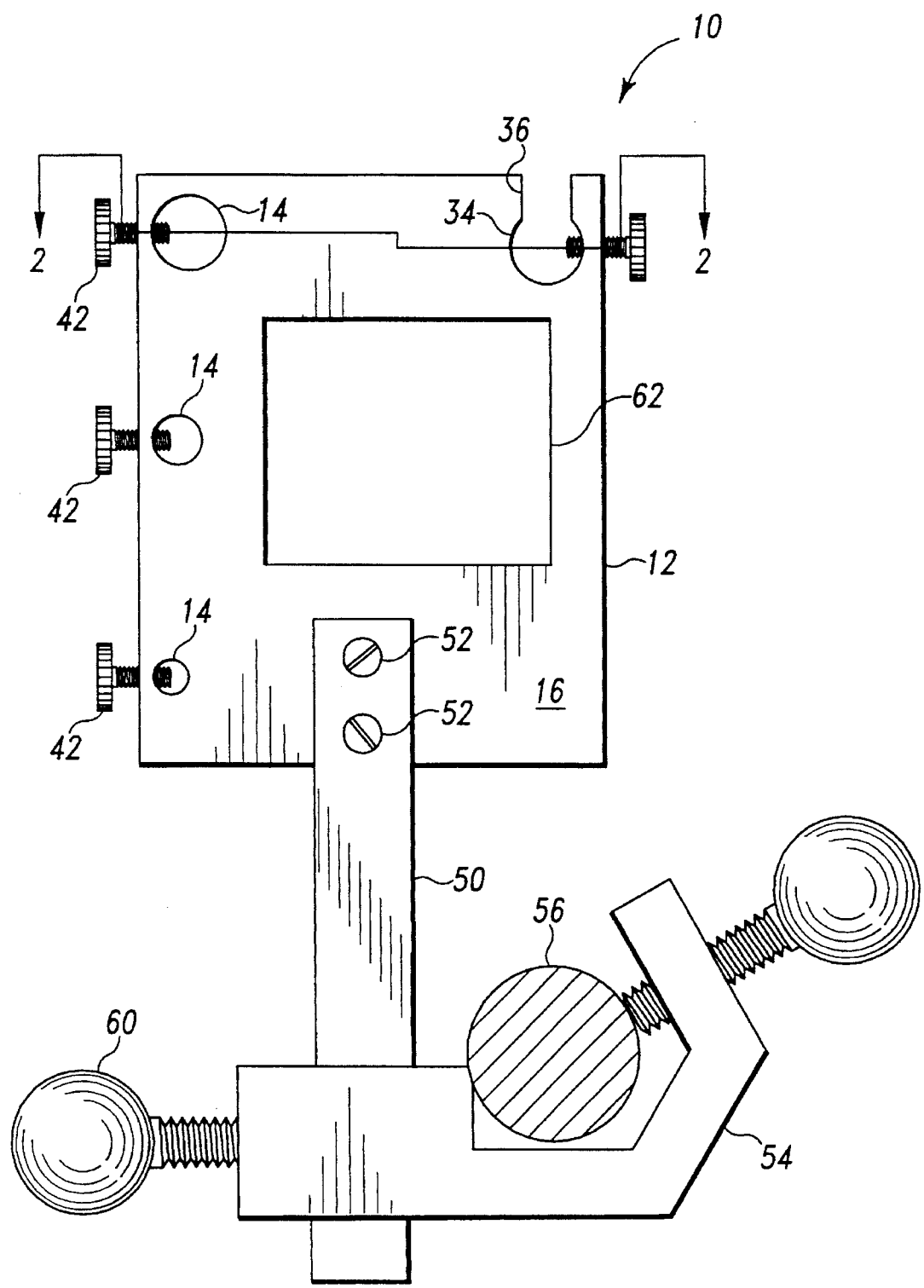
FIG. 1 is a top plan view of a retainer for holding a hypodermic needle and needle cover adjacent an intravenous injection port and associated tubing according to one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to FIG. 1, a hypodermic needle and needle cover retainer 10 is shown. Retainer 10 includes a retention member 12 having a plurality of bores 14 sized for receiving a portion of a needle cover therein. Because hypodermic needles and their associated covers are manufactured having predetermined standard sizes, bores 14 range in diameter according to the diameter of a desired hypodermic needle and needle cover for use therewith. For example, one of the bores is 0.375 in, or approximately 1 cm, in diameter corresponding to a standard hypodermic needle size.

Figure 2:
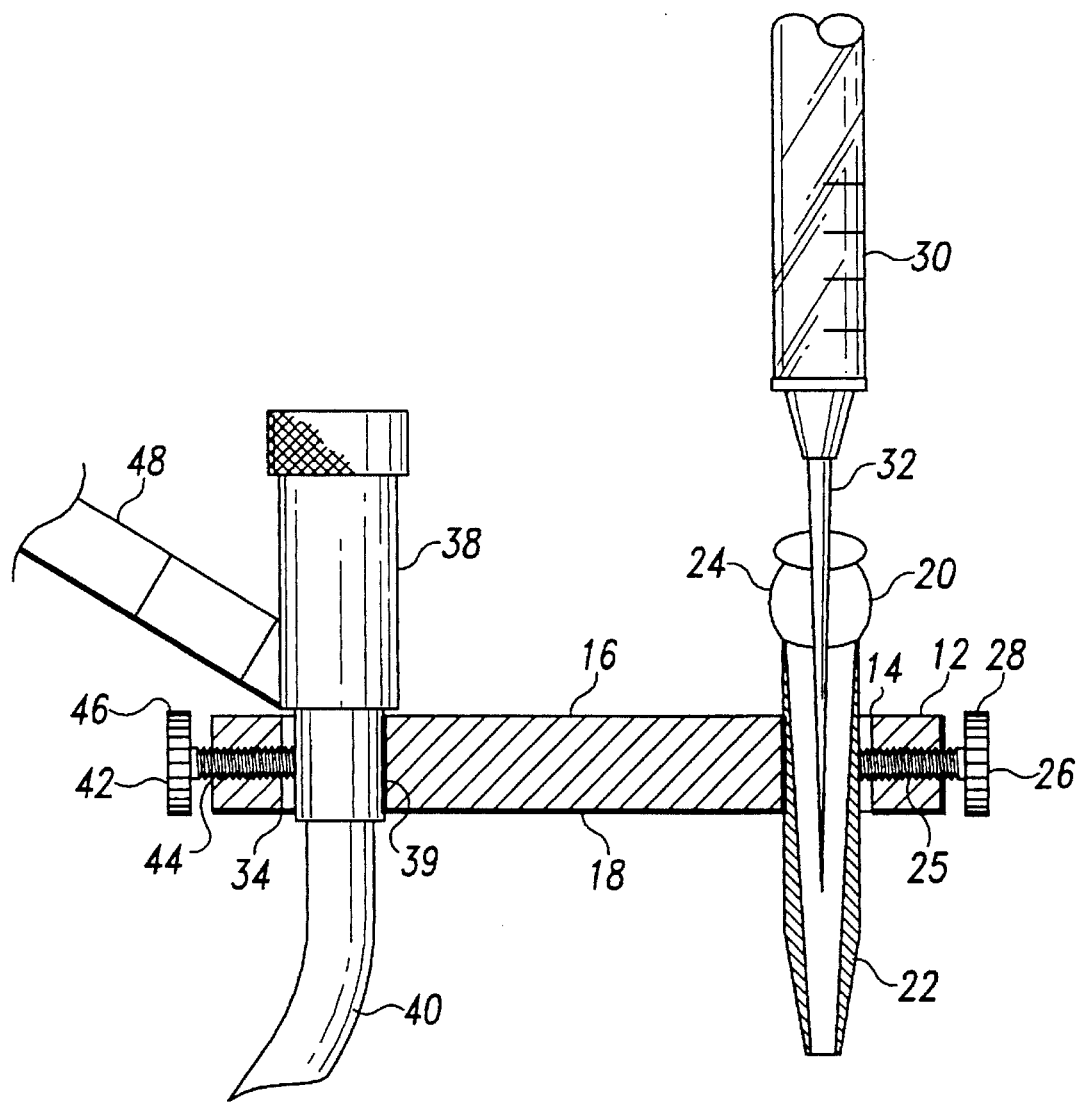
FIG. 2 is a side cross-sectional taken in the direction of line A—A of the hypodermic needle and needle cover retainer of FIG. 1 shown holding a needle cover and intravenous injection port.

Referring now also to FIG. 2, retention member 12 is a substantially flat plate having a top surface 16 and bottom surface 18. Bores 14 extend through retention member 12 between the top and bottom surfaces so as to support a needle cover 20 with a portion 22 of needle cover extending below bottom surface 18. In FIG. 2, needle cover 20 is shown having a collar 24 which has a diameter greater than that of bore 14 to prevent needle cover 20 from falling through retention member 12. However, bore 14 may be tapered or otherwise sized relative to needle cover 20 to prevent needle cover 20 from falling through retention member 12. Also, because retention member 12 need not be aligned horizontally (see, for example, FIG. 4), needle cover 20 may rest in bore 14 without falling through.

Clamping means are provided for clamping needle cover 20 in bore 14 to hold needle cover in retainer while permitting hypodermic needle to be withdrawn from needle cover. Retention member 12 includes a threaded hole 25 extending from bore 14 external of the retention member. Fastener 26 is threadably engaged with threaded hole 25 and is adjustable relative to the retention member. Fastener 26 is preferably a manually adjustable thumb screw having a ridged or knurled portion 28 facilitating manual hand adjustment. When rotated clockwise, fastener 26 adjusts inwardly relative the retention member to extend into bore 14 and contact needle cover 20 to apply a clamp load which clamps needle cover 20 within bore 14. When rotated counter-clockwise, fastener 26 adjusts outwardly relative the retention member to release the clamp load.

In usage of retainer 10, a hypodermic needle 30 having needle cover 20 thereon to protect against inadvertent needle prick injuries is inserted in bore 14 with a portion 22 of needle cover 20 extending below bottom surface 18. Hypodermic needle cover 20 is preferably advanced into bore 14 until collar 24 is seated against top surface 16 of the retention member. Fastener 26 is then advanced within the retention member to clamp needle cover 20 in place within bore 14. With the needle cover clamped to the retention member, hypodermic needle 30 is then removed from needle cover 20, thereby exposing needle 32. After usage, hypodermic needle 30 is then reinserted into needle cover 20 to protect against an inadvertent needle prick injury.

As a practical matter, the tendency for needle prick injuries occurring increases with the amount of time that needle 32 is exposed. Therefore, to reduce the exposure of needle 32, retainer 10 locates needle cover 20 adjacent its intended area of usage. Referring back to FIG. 1, retention member 12 also includes a bore 34 sized for receiving a portion of an intravenous injection port therein. Bore 34 can be sized to a variety of standard intravenous injection port diameters including in this embodiment, for example, a diameter of 0.3125 in (0.8 cm).

Because the ends of the intravenous injection tubing associated with the injection port are oftentimes inaccessible, a slot 36 is disposed in retention member 12 for laterally engaging the tubing. Slot 36 extends between top surface 16 and bottom surface 18 and from bore 34 external of retention member 12. Slot 36 is sized for receiving a portion of intravenous tubing therethrough and, as such, is sized corresponding to a standard intravenous tubing size. For example, in this embodiment slot 36 is 0.25 in wide (0.635 cm).

In FIG. 2, a portion 39 of intravenous injection port 38 is shown received in bore 34 of retention member 12 and having intravenous tubing 40 extending below bottom surface 18. A fastener 42 is threadably engaged with a threaded hole 44 extending from bore 34 external of retention member 12. Similar to fastener 26, fastener 42 is a manually adjustable thumb screw having a ridged or knurled portion 46 facilitating manual adjustment. Intravenous injection port 38 includes a sleeve 48 through which a hypodermic needle may be inserted to administer a prescribed dosage of medication into the injection port and tubing.

In usage of retainer 10, injection port 38 is elevated above top surface 16 so that intravenous tubing 40 can engage with and slide through slot 36. When injection port 38 is aligned with bore 34, injection port 38 is lowered into bore 34 and clamped therein by advancing fastener 42 into contact with portion 39 of the injection port.

As shown in FIG. 2, with both the intravenous injection port 38 and the needle cover 20 clamped within bores 34 and 14, respectively, of retention member 12, retainer 10 minimizes the time needle 32 is exposed to allow safe, repeated administration of unit doses of medication. Between doses of medication, retainer 10 acts as a hypodermic needle support, wherein the syringe of hypodermic needle 30 is held in place in close proximity to the intravenous tubing with needle 32 protected by cover 20.

Referring back to FIG. 1, means for remotely locating retention member 12 is provided by an extension 50. Extension 50 attaches to retention member 12 via fasteners 52. Extension 50 is slidably received in a mounting bracket 54, wherein bracket 54 adjustably locates retainer 10 relative to a vertical intravenous equipment support pole 56. Mounting bracket 54 includes an adjustable clamp 58 threadably engaged therein, wherein rotation of clamp 58 advances the clamp into contact and applies a clamp load to fixedly locate mounting bracket 54 relative pole 56. Similarly, adjustable clamp 60 is threadably engaged with mounting bracket 54 for locking extension 50 in place therein. As such, mounting bracket 54 and retainer 10 are adjustable vertically along intravenous pole 56 via clamp 58, and retainer 10 is adjustable horizontally relative mounting bracket 54 via clamp 60. Retention member 12 also incorporates on top surface 16 a legend 62 on which are printed instructions regarding, for example, the equipment corresponding to retainer 10 and its usage.

Figure 3:
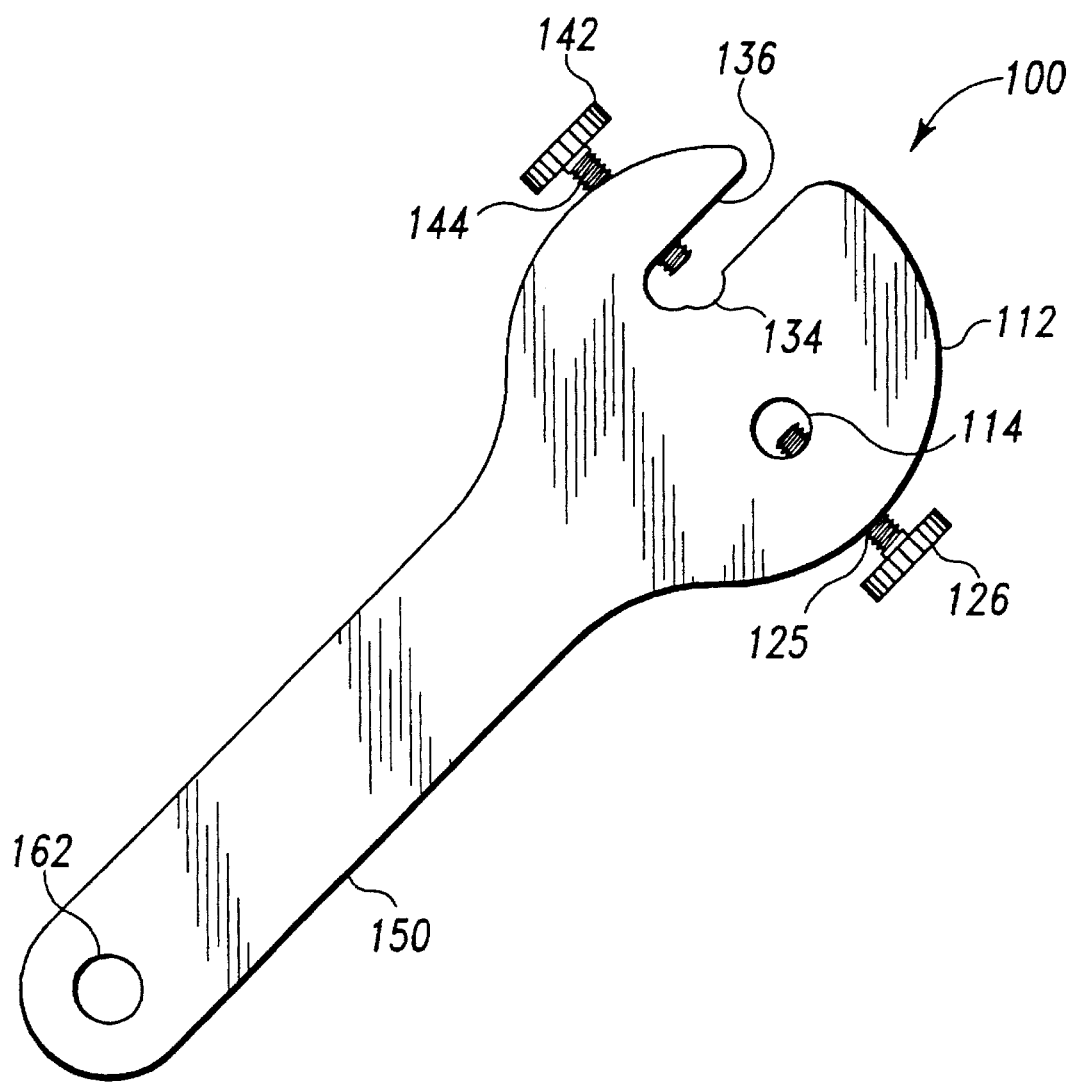
FIG. 3 is a top plan view of a retainer for holding a hypodermic needle and needle cover adjacent an intravenous injection port and associated tubing according to another embodiment of the present invention.

Referring now to FIG. 3, a hypodermic needle and needle cover retainer 100 is shown. In this embodiment, retainer cover 100 is portable and adapted for use by a single hand of a user. Similar to retainer 10, retainer 100 employs a bore 114 sized for receiving a portion of a needle cover therein. Retainer 100 employs a wrench-like form with retention member 112 as the head end and handle 150 providing means for locating retention member 112 remote from the user. A bore 134 corresponding to intravenous injection port 38 and a slot 136 corresponding to intravenous tubing 40 are similarly provided in retention member 112. Thumb screws 126 and 142 provide clamping means for clamping the needle cover and intravenous injection port in bores 114 and 134, respectively.

To facilitate one-handed usage of the retainer 100, threaded holes 125 and 144, which adjustably receive thumb screws 126 and 142 therein, are disposed in retention member 112 to position the thumb screws relative the handle 150 so that a user can with one hand manually adjust the thumb screws while holding handle 150. The direction of rotation of the thumb screws required to apply clamp loads may be switched from clockwise to counter-clockwise as required to facilitate both left hand and right hand usage. Handle 150 also includes a key chain or key ring hole 162 so that retainer 100 can be easily carried on the user's person.

Retainers 10 and 100 are embodiments of needle and needle cover retainers which allow medical personnel to safely recap hypodermic needles without directly touching the needle cover. After recapping, the recapped assembly can be removed with the needle cover in place by simply unlocking the assembly therefrom. As such, both hospital personnel and waste disposal personnel are protected against inadvertent needle prick injuries. Furthermore, by locating the hypodermic needle adjacent its intended area of usage, exposure of the uncovered needle is reduced. Because of their simple design and ease of usage, both retainers 10 and 100 are inexpensively manufactured and readily accepted for re-using hypodermic needles. Furthermore, variations on their design can be adapted for use with other medical equipment.

Figure 4:
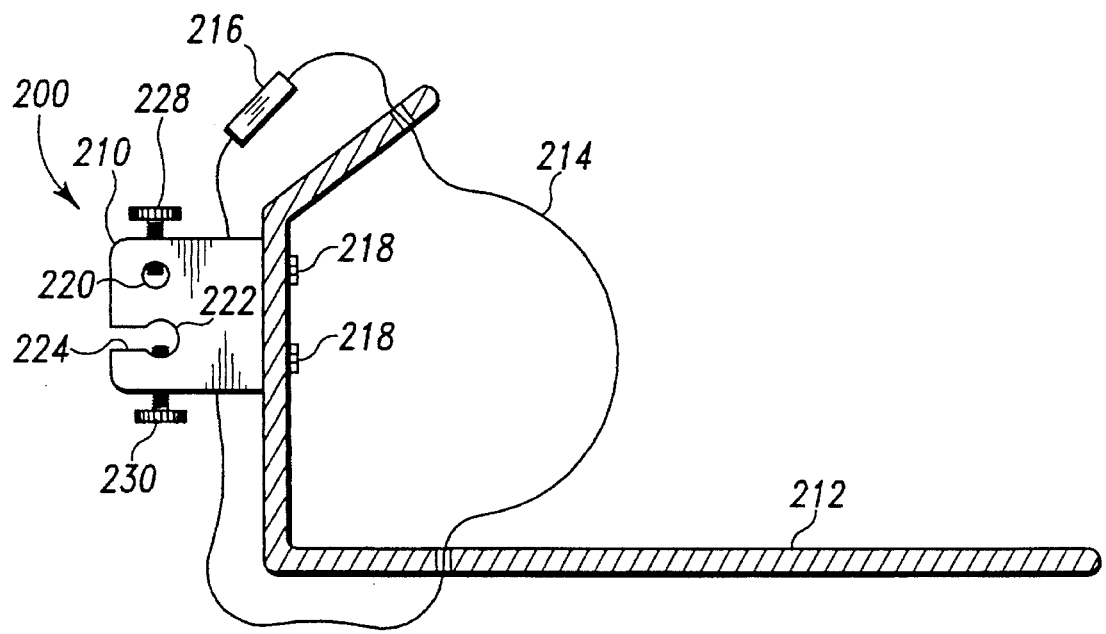
FIG. 4 is an elevational partial cross-sectional view of a retainer, fastened to a restraint, for holding a hypodermic needle and needle cover adjacent an intravenous injection port and associated tubing according to still another embodiment of the present invention.

For example, referring now to FIG. 4 a retainer 200 is shown fastened to a restraint device 212. Restraint 212 includes an adjustable band 214 for restraining, for example, an arm therein. Band 214 adjusts via a standard adjustable buckle 216. Retainer 200 attaches to restraint 212 via fasteners 218. Retainer 200 includes a retention member 210 having a bore 220 sized for receiving a needle cover and bore 222 and slot 224 sized for receiving an intravenous injection port and associated tubing. Both bores extend horizontally through retention member 210 and include adjustable clamps 228 and 230 for clamping the needle cover and intravenous injection port, respectively, therein.

Figure 5:
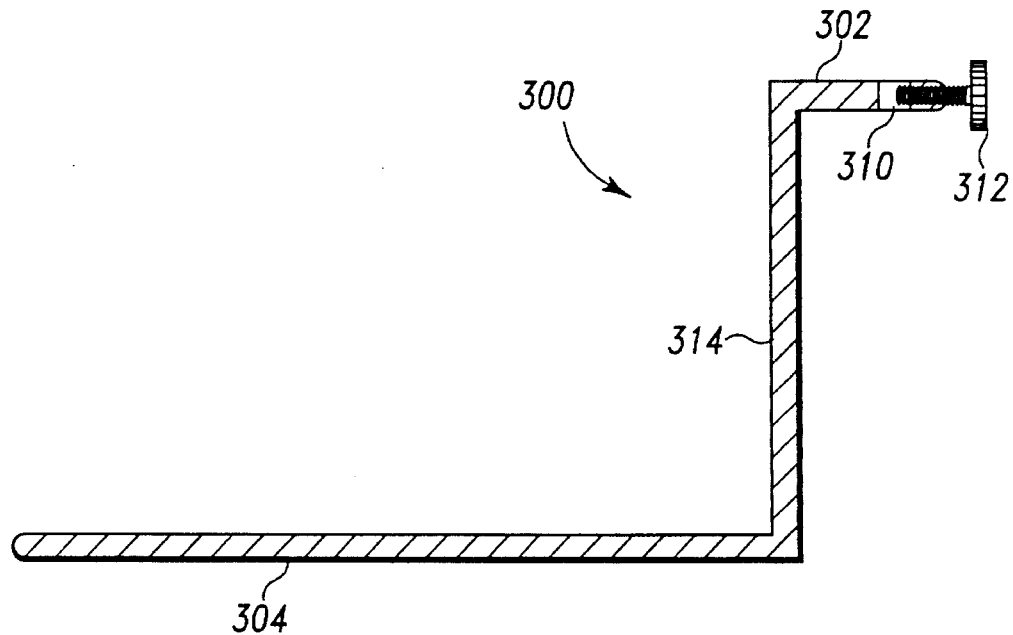
FIG. 5 is a front elevational view of retainer having a top member elevated above a bottom member according to still yet another embodiment of the present invention, wherein the top member is adapted for holding a hypodermic needle and needle cover adjacent an intravenous injection port and associated tubing.
Figure 6:
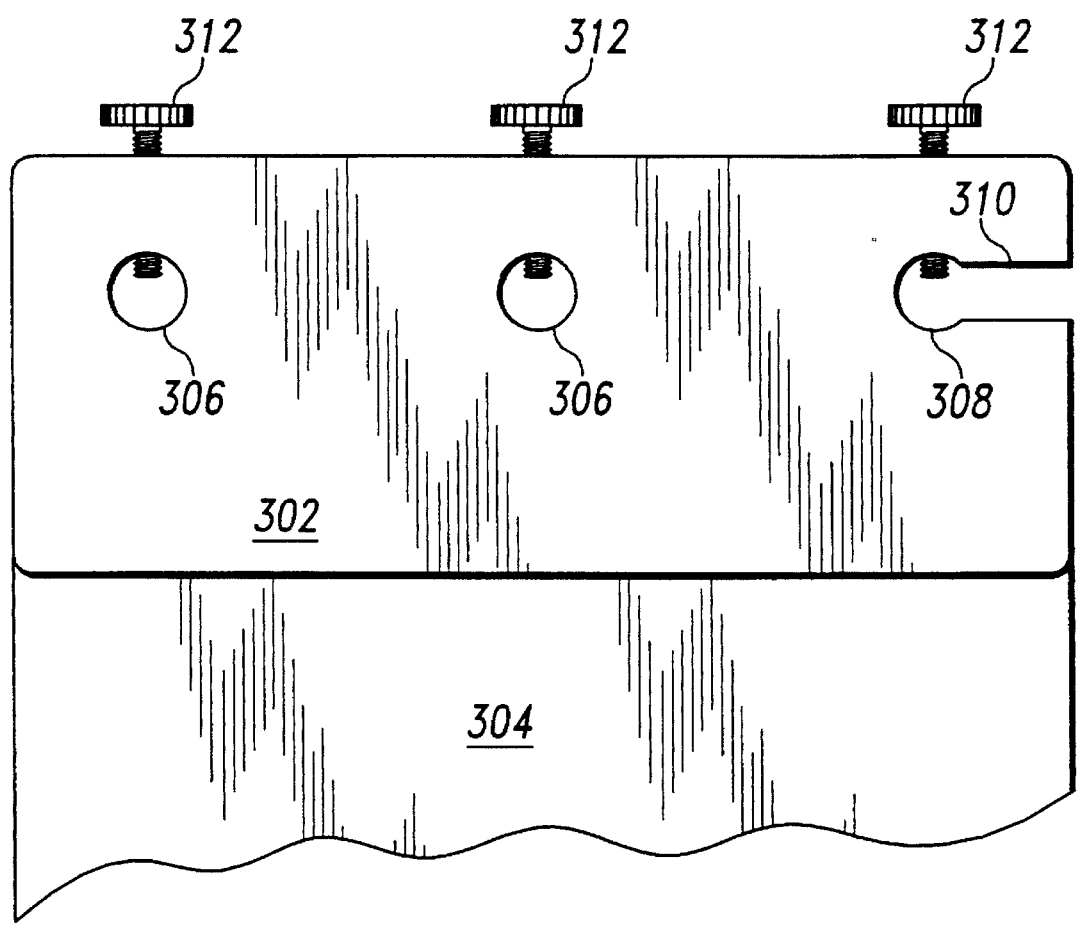
FIG. 6 is a partial top plan view of the retainer of FIG. 5.

Referring now to FIG. 5, still yet another embodiment is shown, wherein the retention member is adapted for use, as one example, in conjunction with a mattress. Retainer 300 includes a horizontal top member 302 and a horizontal bottom member 304. Referring also to FIG. 6, horizontal top member includes bores 306 for receiving a needle cover therein and bore 308 and slot 310 for receiving an intravenous injection port and associated tubing. Fasteners 312 provide clamping means for clamping corresponding needle covers and intravenous injection port in bores 306 and 308, respectively. Referring back to FIG. 5, an upstanding vertical support member 314 is attached between ends of the top and bottom members to elevate the top member above the bottom member. In usage of retainer 300, bottom member 304 slides underneath a mattress with vertical member 314 elevating top surface 302 approximately level with the top of the mattress. The weight alone of the mattress holds retainer 300 in place and, as such, retainer 300 is easily portable between hospital beds.

With the above embodiments of the present invention, by facilitating the reuse of hypodermic needles, repeated administration of small doses of medication can be accomplished without increasing the risk of needle stick injury. Because the above embodiments manipulate both the needle cover and the intravenous infusion port and tubing, the needle and needle cover are maintained in close proximity to the intravenous tubing, thereby further reducing the exposure of the needle and the risk of needle recapping injuries. Also, since the needle retainer can hold and support both the hypodermic needle and the needle cover, a hypodermic needle may be preloaded with medication and supported by the retainer to be readily available in an emergency situation. Other mounting arrangements facilitating easy usage of the above embodiments include VELCRO* or additional clamp means engaged with the retainer for clamping the retainer to a table. Also contemplated, to facilitate usage in less than optimal lighting conditions, are lighting means for exposing the needle cover bore or intravenous injection port bore. For example, the retention member may be constructed of fluorescent plastic to provide a "glow in the dark" lighting scheme. With all of the above embodiments, the needle retainers can be made of autoclavable plastic or stainless steel for ready sterilization.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. In combination, a hypodermic needle cover, an intravenous injection port, and a device for facilitating the safe handling of hypodermic needles and intravenous injection ports, said combination comprising:

a hypodermic needle cover;

an intravenous injection port including an intravenous injection port hub and associated tubing connected thereto; and a substantially flat plate having a top and a bottom surface and a peripheral edge thereabout, said plate defining:

a needle cover retaining bore extending through said plate between said top and bottom surfaces of said plate, said needle cover retaining bore being sized for partially receiving and seating a needle cover therein;

an intravenous injection port bore extending through said plate between said top and bottom surfaces of said plate, said intravenous injection port bore being sized for partially receiving and seating an intravenous injection port hub therein;

an elongated slot extending through said plate between said top and bottom surfaces of said plate and extending from said intravenous injection port bore to the periphery of said plate, said slot being sized so as to permit transverse passage of said intravenous injection port's associated tubing therethrough but yet to prevent transverse passage of the port hub through said slot; and wherein said needle cover is partially received and seated within said needle cover retaining bore; and wherein said intravenous injection port hub is partially received and seated within said intravenous injection port bore with transverse movement of said intravenous injection port hub through said elongated slot being prevented owing to the reduced size of said slot relative to said intravenous injection port hub.

2. A method for securely seating an intravenous injection port, the intravenous injection port including a hub and associated tubing connected thereto, said method comprising the steps of:

(a) providing a substantially flat plate having a top and a bottom surface and a peripheral edge thereabout and having an intravenous injection port bore extending through the plate between the top and bottom surfaces of the plate, the intravenous injection port bore being sized for partially receiving and seating an intravenous injection port hub therein, and an elongated slot extending through the plate between the top and bottom surfaces of the plate and extending from the intravenous injection port bore to the periphery of the plate, the slot being sized so as to permit transverse passage of the intravenous injection port's associated tubing therethrough but yet to prevent transverse passage of the port hub through the slot;

(b) sliding the associated tubing of an intravenous injection port through the elongated slot and into said intravenous injection port bore; and (c) moving the hub of the intravenous injection port toward the plate until the hub is partially received and seated within the intravenous injection port bore with transverse movement of the intravenous injection port hub through the elongated slot being prevented owing to the reduced size of the slot relative to the intravenous injection port hub.

* * * * *

UNITED STATES PATENT AND TRADEMARK OFFICE
CERTIFICATE OF CORRECTION

PATENT NO. : 5,556,388

DATED : September 17, 1996

INVENTOR(S) : Frederick C. Johlin, Jr.

It is certified that error appears in the above-identified patent and that said Letters Patent is hereby corrected as shown below:

Item [54], of the title page, please delete the slash between "INJECTION" and "PORTS".

In column 1, line 4, please delete the slash between "INJECTION" and "PORTS".

In column 2, line 39, please insert --view-- before "taken".

In column 2, line 52, please insert --a-- before "retainer".

Signed and Sealed this

Fourth Day of November, 1997

BRUCE LEHMAN

*Attest:*

*Attesting Officer*  *Commissioner of Patents and Trademarks*